United States Patent [19]

Parsons

[11] 4,237,127
[45] Dec. 2, 1980

[54] 1,2,4,5-TETRAZINES

[75] Inventor: John H. Parsons, Saffron Walden, England

[73] Assignee: Fisons Limited, London, England

[21] Appl. No.: 40,877

[22] Filed: May 21, 1979

[30] Foreign Application Priority Data

May 25, 1978 [GB] United Kingdom ............... 22306/78

[51] Int. Cl.³ .................... C07D 257/02; A01N 43/64
[52] U.S. Cl. ..................... 424/244; 544/179
[58] Field of Search ........................ 544/179; 424/244

[56] References Cited

U.S. PATENT DOCUMENTS

| 3,166,399 | 1/1965 | Lutz et al. ............................. 544/179 |
| 3,860,588 | 1/1975 | Pilgrim et al. ......................... 544/179 |
| 3,860,589 | 1/1975 | Pilgrim et al. ......................... 544/179 |

FOREIGN PATENT DOCUMENTS

| 49-4532 | 2/1974 | Japan ....................................... 544/179 |
| 498300 | 6/1976 | U.S.S.R. . |

Primary Examiner—John M. Ford
Attorney, Agent, or Firm—Wenderoth, Lind & Ponack

[57] ABSTRACT

The substituted tetrazines of the formula:

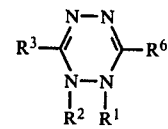

and of the formula:

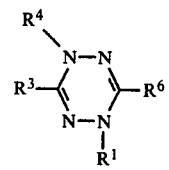

wherein: $R^1$, $R^2$ and $R^4$ each represent hydrogen, phenyl, alkyl of 1 to 6 carbon atoms, or alkenyl or alkynyl of 3 to 6 carbon atoms, each of which may be unsubstituted or substituted by one or more halogen atoms, hydroxy groups, cyano groups, carboxy groups, alkoxycarbonyl groups of 2 to 5 carbon atoms, or alkoxy groups of 1 to 4 carbon atoms; or $R^1$ and $R^2$ together represent a single bond; $R^3$ represents alkyl of 1 to 6 carbon atoms, cycloalkyl of 3 to 7 carbon atoms, phenyl or phenylalkyl of 7 to 10 carbon atoms, each of which may be unsubstituted or substituted by one or more halogen atoms, alkyl or alkoxy groups of 1 to 6 carbon atoms, nitro groups, cyano groups, mercapto groups, or alkylmercapto groups of 1 to 4 carbon atoms; and $R^6$ represents a phenyl group substituted in at least the 2-position by fluorine, chlorine, bromine or iodine; are effective to combat acarids and their eggs.

14 Claims, No Drawings

1,2,4,5-TETRAZINES

This invention concerns certain tetrazines which are active against acarid eggs and larvae, processes for their preparation, compositions containing them and methods of using them.

In one aspect, this invention provides a method of combatting acarids, their eggs or their larvae, which comprises applying to a site either infested or liable to infestation with them an effective amount of one or more substituted tetrazines of the formula:

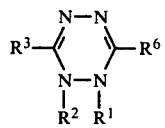

or of the formula:

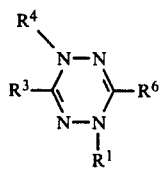

wherein, $R^1$, $R^2$ and $R^4$, which may be the same or different, each represent hydrogen, phenyl, alkyl of 1 to 6 carbon atoms, or alkenyl or alkynyl of 3 to 6 carbon atoms, each of which may be unsubstituted or substituted by one or more halogen atoms, hydroxy groups, cyano groups, carboxy groups, alkoxycarbonyl groups of 2 to 5 carbon atoms or alkoxy groups of 1 to 4 carbon atoms; or $R^1$ and $R^2$ together represent a single bond; $R^3$ represents alkyl of 1 to 6 carbon atoms, cycloalkyl of 3 to 7 carbon atoms, phenyl, or phenylalkyl of 7 to 10 carbon atoms, each of which may be unsubstituted or substituted by one or more halogen atoms, alkyl or alkoxy groups of 1 to 6 carbon atoms, nitro groups, cyano groups, mercapto groups or alkylmercapto groups of 1 to 4 carbon atoms; and $R^6$ represents a phenyl group substituted in at least the 2-position by fluorine, chlorine, bromine or iodine.

In another aspect, this invention provides an acaricidal, larvicidal or ovicidal composition which comprises one or more compounds of formula I or formula II as defined hereinbefore in association with a suitable carrier and/or surface active agent.

In a further aspect, this invention provides per se the compounds of formulae I and II with the proviso that, in the compounds of formula I wherein $R^6$ represents 2-fluorophenyl, when $R^1$ and $R^2$ represent a single bond, $R^3$ does not represent methyl, trifluoromethyl or 2-fluorophenyl, and when $R^1$ and $R^2$ both represent hydrogen, $R^3$ does not represent trifluoromethyl.

$R^1$, $R^2$ and $R^4$ independently preferably represent hydrogen or alkyl of 1 to 6, especially 1 to 4, carbon atoms, which is preferably unsubstituted, for example methyl, ethyl, n-propyl, isopropyl or t-butyl. In the compounds of formula I, hydrogen is especially preferred for one of $R^1$ and $R^2$, the other preferably representing alkyl, especially methyl or ethyl. In the compounds of formula II, $R^1$ and $R^4$ each preferably represent alkyl, especially methyl or ethyl.

When $R^1$ and/or $R^2$ and/or $R^4$ represents a substituted alkyl group, however, it is preferably substituted by hydroxy (e.g. 2-hydroxyethyl), but each may represent, for example, 2-chloroethyl, chloromethyl, cyanomethyl, carboxymethyl, methoxycarbonyl-methyl or 2-methoxyethyl if desired.

Preferred alkenyl and alkynyl groups which $R^1$, $R^2$ may represent are allyl and propargyl, which are preferably unsubstituted.

When $R^1$ and/or $R^2$ and/or $R^4$ represents phenyl, it is preferably unsubstituted.

When $R^3$ represents alkyl of 1 to 6 carbon atoms, it may, for example, be methyl, ethyl, n-propyl, isopropyl or, especially, t-butyl. Preferred cycloalkyl groups which $R^3$ may represent include cyclopentyl and cyclohexyl. When $R^3$ represents alkyl or cycloalkyl it is preferably unsubstituted. When substituted, however, it is preferably substituted by one or more halogen atoms, cyano groups or hydroxy groups, specific preferred substituted groups being trifluoromethyl, chloromethyl, cyanomethyl, trichloromethyl and 2-hydroxyethyl.

When $R^3$ represents phenyl, as is preferred, it is desirably substituted by one or more halogen atoms, C 1 to 4 alkyl or alkoxy groups or nitro groups. The group is preferably mono-substituted, specific preferred groups being 2-chlorophenyl, 2-fluorophenyl, 2-bromophenyl, 3-methylphenyl and 4-methylphenyl.

When $R^3$ represents a phenylalkyl group, it is preferably benzyl which is desirably unsubstituted or monosubstituted by halogen, e.g. 4-chlorobenzyl.

$R^6$ preferably represents 2-chlorophenyl or 2-bromophenyl, especially 2-chlorophenyl, or a further substituted derivative thereof, for example 2,4-dichlorophenyl or 2-chloro-4-methylphenyl.

$R^3$ and $R^6$ are preferably identical.

Where $R^4$ in formula II represents hydrogen, the compounds are of course also compounds of formula I (where $R^2$ represents hydrogen).

In a preferred group of compounds of formula I, $R^1$ and $R^2$ both represent hydrogen, or together represent a single bond, or one represents hydrogen while the other represents methyl, $R^6$ represents 2-chlorophenyl or 2-bromophenyl, and $R^3$ represents t-butyl, phenyl, 2-chlorophenyl, 2-fluorophenyl, 2-bromophenyl, 3-methylphenyl or 4-methylphenyl.

Specific preferred compounds of this invention are those of the Examples provided hereinafter. Particular mention may be made however of the most preferred compounds 3,6-bis(2-chlorophenyl)-1,2-dihydro-1-methyl-1,2,4,5-tetrazine and 3,6-bis(2-chlorophenyl)-1,2,4,5-tetrazine.

In another aspect, this invention provides a process for the preparation of the compounds of formula I wherein $R^1$ and $R^2$ represent other than a single bond, in which process a substituted azine of the formula:

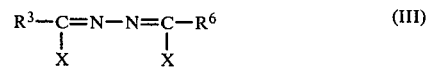

(wherein $R^3$ and $R^6$ are as defined hereinbefore and each X represents a leaving group) is reacted with a hydrazine of the formula:

(wherein $R^1$ and $R^2$ are as defined hereinbefore but do not together represent a bond) to give the desired compound.

The reaction is conveniently carried out at an elevated temperature, e.g. from 30° to 100° C., especially 50° to 80° C., in an appropriate solvent medium, e.g. an alkanol, e.g. ethanol, an ether, e.g. tetrahydrofuran, or a hydrocarbon.

X preferably represents halogen (especially chlorine or bromine), cyano, or C 1 to 4 alkoxy (especially methoxy).

The reaction of compounds of formulae III and IV appears to give rise (when $R^3$ is not the same as $R^6$ and $R^1$ is not the same as $R^2$) to a mixture of isomeric products. The present invention extends of course to cover the isomeric structures which may be produced.

The substituted azines of formula III employed as starting materials in the above process may themselves be prepared by a process in which a compound of the formula:

$$R^3—A—R^6 \qquad (V)$$

(wherein $R^3$ and $R^6$ are as defined hereinbefore, and A represents —CONH—NHCO—, —CONH—N=CH—, —CH=N—NHCO— or —CH=N—N=CH—) is halogenated to give the desired compound of formula III wherein X represents halogen, and the product is, if desired, reacted with an anion forming compound to give the corresponding compound where X represents a different leaving group.

When A represents —CONH—NHCO—, the halogenating agent is preferably a phosphorus pentahalide, especially phosphorus pentachloride or phosphorus pentabromide, and is preferably employed in a suitable solvent medium, for example a hydrocarbon or halogenated hydrocarbon, e.g. carbon tetrachloride or o-dichlorobenzene. The reaction is conveniently effected at elevated temperature, e.g. from 70°–150° C., especially from 90°–110° C.

When A represents —CONH—N=CH— or —CH=N—NHCO—, the halogenation is desirably achieved in two stages by reaction of the compound of formula V with a thionyl halide, especially thionyl chloride, and with the halogen itself, especially chlorine.

When A represents —CH=N—N=CH—, the halogenation is conveniently achieved in a single step reaction with the desired halogen in an appropriate solvent medium, for example acetic acid.

The compounds of formula V where A represents —CONH—NHCO— may be prepared by a process in which a hydrazide of the formula $R^3CONHNH_2$ is reacted with a compound of the formula $R^6COY$, where $R^3$ and $R^6$ are as defined hereinbefore and Y represents halogen (especially chlorine or bromine), hydroxy, C 1 to 6 alkoxy or a group $R^6COO$—, to give the desired compound.

The reaction is preferably carried out in the presence of a base, e.g. an alkali-metal hydroxide or carbonate, e.g. sodium hydroxide or carbonate, or an amine, e.g. triethylamine.

The reaction is conveniently effected at a temperature of from 5° to 50° C.

Where A represents —CONH—NHCO— and $R^3$ is the same as $R^6$, the compounds of formula V may be prepared directly by reaction of a halide of formula $R^3$COHal where Hal represents halogen, especially chlorine or bromine, with hydrazine.

This reaction is desirably effected in a suitable solvent for the product, e.g. water, and in the presence of a base, e.g. an alkali-metal base, e.g. sodium hydroxide. The temperature employed is preferably 5°–30° C.

The compounds of formula V where A represents —CH=N—N=CH— and $R^3$ and $R^6$ are identical may be prepared by a process in which an aldehyde of the formula $R^3CHO$ where $R^3$ is as defined hereinbefore is reacted with hydrazine in a suitable solvent medium to give the desired compound.

The solvent is preferably water and/or an alkanol, e.g. aqueous ethanol, and the reaction is preferably carried out at a temperature of from 5° to 30° C., especially 10° to 20° C.

The compounds of formula V where A represents —CONH—N=CH— or —CH=N—NHCO— may be prepared by reaction of a hydrazide of the formula $R^3CONHNH_2$ or $R^6CONHNH_2$ with an aldehyde respectively of the formula $R^6CHO$ or $R^3CHO$.

The hydrazides of formula $R^3CONHNH_2$ employed as starting materials may be prepared by conventional processes, for example by reaction of hydrazine with one molar proportion of the appropriate ester $R^3COOR$ where R represents alkyl, especially of 1 to 4 carbon atoms.

The compounds of formula I wherein $R^1$ and $R^2$ together represent a single bond may be prepared from the corresponding compounds of formula I wherein $R^1$ and $R^2$ both represent hydrogen by reaction thereof with a suitable oxidising agent.

The preferred oxidising agent is an alkali-metal nitrite, e.g. sodium nitrite, employed in the presence of an acid, and the reaction is desirably carried out in an appropriate solvent medium which is inert under the reaction conditions employed, e.g. glacial acetic acid. However, many other oxidising agents may be appropriate, for example nitric acid, hydrogen peroxide, bromine or isoamyl nitrite, each desirably employed in a suitable solvent medium, e.g. acetic acid, an alkanol for example ethanol, or an optionally halogenated hydrocarbon, e.g. carbon tetrachloride or chloroform.

The reaction is conveniently carried out at a temperature of from 5° to 30° C., preferably 10° to 20° C.

In another aspect, this invention provides a process for the preparation of the compounds of formula II wherein a thiadiazolium salt of the formula:

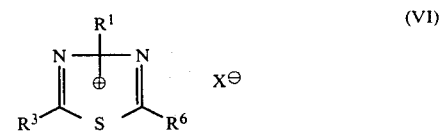

(VI)

(wherein $R^1$, $R^3$ and $R^6$ are as defined hereinbefore) and $X^-$ represents an anion, is reacted with a hydrazine of formula $R^4NHNH_2$ (wherein $R^4$ as defined hereinbefore) to give the desired compound.

The reaction is desirably effected in the presence of a solvent, e.g. an alkanol such as ethanol, and is preferably carried out at a temperature of from 20° C. to the reflux temperature, e.g. 100° C.

$X^-$ may represent any suitable anion, but is preferably halogen, especially chlorine, sulphate or p-toluensulphonate.

The thiadiazolium salts of formula VI may themselves be prepared by a process in which a corresponding thiadiazole of the formula:

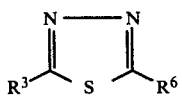

(wherein $R^3$ and $R^6$ are as defined hereinbefore) is reacted with the appropriate compound of formula $R^1X$ to give the desired compound.

The reaction is preferably effected in an appropriate solvent medium, e.g. an alkanol such as ethanol, and at a temperature of from 60° C. to the reflux temperature, e.g. 180° C.

The thiadiazoles of formula VII may themselves be prepared either by reaction of a compound of formula V wherein A represents —CONH—NHCO— with phosphorous pentasulphide, or by reaction of a compound of formula III with a sulphide (especially phosphorous pentasulphide) or hydrosulphide to give the desired compound.

The reactions involving phosphorous pentasulphide are desirably effected in an appropriate solvent medium, and desirably also in the presence of a tertiary organic base. The base may act as the solvent medium, and may for example be pyridine, triethylamine or dimethylaniline, and the reaction is desirably effected at a temperature of from 80° C. to the reflux temperature, e.g. 120° C.

The sulphide or hydrosulphide employed in the reaction with the compound of formula III may alternatively be an alkali-metal sulphide or hydrosulphide, e.g. sodium sulphide or potassium hydrosulphide, and the reaction is desirably effected in an appropriate solvent medium, e.g. an alkanol, e.g. ethanol, or a polar solvent, e.g. dimethylformamide, and at a temperature of from 5° C. to the reflux temperature, e.g. 80° C.

In a further aspect, this invention provides a process for the preparation of the compounds of formula II in which $R^3$ and $R^6$ are identical and $R^1$ and $R^4$ are identical, wherein a compound of the formula:

$$R^6CH=N.NHR^4 \qquad (VIII)$$

(where $R^4$ and $R^6$ are as defined hereinbefore) is subjected to the action of an oxidising agent to give the desired compound.

The oxidising agent is conveniently a halogen, e.g. iodine, or an alkali-metal hypochlorite or ferricyanide, especially sodium hypochlorite or ferricyanide, and the reaction is conveniently effected in a suitable solvent, e.g. pyridine, and at a temperature of from 60° to 120° C.

The compounds of formula II in which $R^3$ and $R^6$ are identical and $R^1$ and $R^4$ are identical may alternatively be prepared by a process in which a compound of the formula:

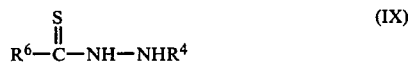

(wherein $R^4$ and $R^6$ are as defined hereinbefore) is subjected to the action of an alkylating agent in the presence of an alkali-metal base, e.g. sodium hydroxide or sodium carbonate.

The alkylating agent is conveniently a haloacetic acid, e.g. iodoacetic acid, or a dialkyl sulphate, e.g. dimethyl sulphate, and the reaction is desirably effected in a suitable solvent, e.g. an alkanol such as ethanol. The temperature employed is desirably from 5° to 80° C.

The compounds of formula II wherein $R^1$ and $R^4$ are other than hydrogen, $R^3$ and $R^6$ are identical and $R^1$ and $R^4$ are identical, may be prepared by a process in which a compound of the formula:

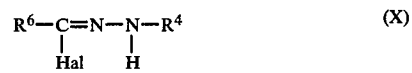

(wherein $R^4$ and $R^6$ are as defined hereinbefore and Hal represents halogen) is dimerised in the presence of a base in an appropriate solvent medium to give the desired compound.

The reaction is desirably effected in a suitable solvent, especially a polar aprotic solvent such as acetonitrile or dimethylformamide, and at elevated temperature, e.g. 50° C. to reflux.

Hal preferably represents chlorine.

The base is conveniently a tertiary amine, e.g. triethylamine, and the solvent is preferably a polar solvent, e.g. acetonitrile.

The tetrazines of formula I and formula II are of general use as acaricides and/or ovicides. They are of particular use against the eggs and larvae of acarids, particularly the eggs of the red spider mite, *Tetranychus cinnabarinus,* but also against the eggs and larvae of other mite species, e.g. *Tetranychus urticae, Panonychus ulmi, Phyllocoptrata oleivora, Eutetranychus banksi, P. citri* and *T. medanieli.* They are normally employed in the foam of compositions.

The compositions of the invention will normally be produced initially as formulations containing from 0.5 to 99%, preferably from 0.5 to 85% by weight, more usually from 10 to 50% by weight, of the active compounds, which are diluted if necessary before application to the locus to be treated such that the concentration of active ingredient in the formulation applied is from 0.05 to 5% by weight.

The substituted tetrazines of formula I and formula II are generally water insoluble and may be formulated in any of the ways commonly adopted for insoluble compounds.

For example, they may be dissolved in a water immiscible solvent, for example a high boiling hydrocarbon, as carrier, suitably containing dissolved emulsifying agents so that the composition acts as a self-emulsifiable oil on addition to water.

The substituted tetrazines may alternatively be admixed with a wetting agent with or without a solid carrier to form a wettable powder which is soluble or dispersible in water, or may be mixed with just a solid carrier to form a solid product.

An aqueous suspension concentrate may alternatively be prepared by grinding the compounds with water, a wetting agent and a suspending agent.

Solid carriers with which the substituted tetrazines may be incorporated include clays, sands, talc, mica or solid fertilizers, such products either comprising dust or larger particle size materials.

The surface active agents used may comprise anionic surface active agents, for example mono- or di-esters of phosphoric acid with fatty alcohol ethoxylates or salts of such esters, fatty alcohol sulphates such as sodium dodecyl sulphate, ethoxylated fatty alcohol sulphates, ethoxylated alkylphenol sulphates, lignin sulphonates, petroleum sulphonates, alkylaryl sulphonates such as alkyl-benzene sulphonates or lower alkyl-naphthalene sulphonates, salts of sulphonated naphthalene-formaldehyde condensates, salts of sulphonated phenol-formaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The surface active agents may also comprise non-ionic agents, for example condensation products of fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quarternary ammonium compounds such as cetyl trimethyl-ammonium bromide, or ethoxylated tertiary fatty amines.

Preferred surface active agents include ethoxylated fatty alcohol sulphates, lignin sulphonates, alkyl-aryl sulphonates, salts of sulphonated naphthalene-formaldehyde condensates, salts of sulphonated phenol-formaldehyde condensates, sodium oleoyl N-methyltauride, dialkyl sulphosuccinates, alkyl phenol ethoxylates, and fatty alkyl ethoxylates.

The composition may alternatively be in the form of an aerosol composition, suitably using a cosolvent and a wetting agent, in addition to the propellant, which is suitably a polyhalogenated alkane such as dichlorodifluoromethane.

The compositions according to the present invention may contain in addition to the substituted tetrazines other active insecticides, acaricides, ovicides, bactericides and fungicides. It has been found that particular advantages are obtained with mixtures with other acaricides, especially those which combat the motile stages, e.g. amitraz, dicofol, cyhexatin or propargite, and particularly where the compound of formula I or II is one of those exemplified herein, especially 3,6-bis(2-chlorophenyl)-1,2-dihydro-1-methyl-1,2,4,5-tetrazine or 3,6-bis(2-chlorophenyl)-1,2,4,5-tetrazine.

The method of combatting acarids, their eggs or their larvae provided by the present invention may be employed at any site where infestations of such pests are present or are liable to occur. Thus, it may be employed for example on plants or the soil.

Plants which may be treated include food crops, for example, fruit trees and cereals, e.g. apples, pears, apricots, citrus fruits, maize, wheat or barley, beans, sugar beet, potatoes, carrots, or greenhouse crops, e.g. peppers, tomatoes, cucumbers, melons or strawberries.

In their various applications the compounds of formula I and formula II may be used at various rates; thus for example for the treatment of plants for the control of pests on plants the compounds are suitably applied at a rate of about 0.25–16 ounces per acre (17–1120 g per hectare) or at a concentration of 1 to 2000 ppm as appropriate, e.g. 100 to 1000 ppm, and preferably 0.5–4 ounces per acre (35–280 g per hectare). Normally the compounds will be applied to the foliage of plants, but systemic activity has also been observed when applied to the soil around the base of the plants.

The following Examples are given merely to illustrate the present invention. The temperatures given therein are in °C., and parts and percentages are by weight.

EXAMPLE 1

3,6-bis(2-Chlorophenyl)-1,2-dihydro-1-methyl-1,2,4,5-tetrazine (a) N,N'-bis(2-chlorobenzoyl)hydrazine A stirred solution of hydrazine hydrate (25 g) in water (500 ml) was treated dropwise and simultaneously with sodium hydroxide (43.6 g) in water (150 ml) and 2-chlorobenzoyl chloride (180.25 g). The addition over the mixture was stirred at room temperature for 2 hours. The solid was filtered off, washed with acetone/water 1:1 and recrystallised from acetic acid. Yield 97.5 g, m.p. 217°–219°.

(b) bis($\alpha$:2-Dichlorobenzylidene)hydrazine

Phosphorus pentachloride (443.5 g) in 1,2-dichlorobenzene (850 ml) was heated to 110°. N,N'-bis(2-chlorobenzoyl)hydrazine (164.7 g) was added in portions to the stirred solution. The addition over the mixture was stirred and heated at 110° for 1 hour. At the end of this time the excess phosphorus pentachloride and 1,2-dichlorobenzene were distilled off under reduced pressure to leave a viscous oil which solidified. The crude solid was recrystallised from methanol (2x) to give 58.0 g of bis($\alpha$:2-dichlorobenzylidene)hydrazine as a white crystalline solid, m.p. 105°–107°.

(c) 3,6-bis(2-Chlorophenyl)-1,2-dihydro-1-methyl-1,2,4,5-tetrazine

Methyl hydrazine (31.0 g) in ethanol (550 ml) was heated to reflux and treated portionwise with bis($\alpha$:2-dichlorobenzylidene) hydrazine (58.0 g). The addition over the mixture was refluxed for ½ hour.

The ethanol was evaporated in vacuo and the residue washed with water. Recrystallisation from an ethanol/water mixture yielded 37.0 g, m.p. 116°–118°.

EXAMPLES 2–4

The following compounds were prepared by the method of Example 1 but employing the appropriate o-halobenzoyl chloride in stage (a) and the appropriate hydrazine or substituted hydrazine in stage (c).
2. 3,6-bis(2-Chlorophenyl)-1,2-dihydro-1,2,4,5-tetrazine, mp 168°–169° C.
3. 3,6-bis(2-Fluorophenyl)-1,2-dihydro-1-methyl-1,2,4,5-tetrazine, mp 93°–94° C.
4. 3,6-bis(2-Fluorophenyl)-1,2-dihydro-1,2,4,5-tetrazine, mp 145°–148° C.
5. 3,6-bis(2-Chlorophenyl)-1,2-dihydro-1-(2-hydroxyethyl)-1,2,4,5-tetrazine, mp 50°–55° C.

EXAMPLE 6

3-(4-Methylphenyl)-6-(2-chlorophenyl)-1,2-dihydro-1-methyl-1,2,4,5-tetrazine (a) N-(2-chlorobenzoyl)-N'-(4-Methylbenzoyl)hydrazine 2-Chlorobenzhydrazide (38.8 g) was dissolved in sodium hydroxide solution (9.18 g in 125 ml water). The solution was stirred and 4-methylbenzoyl chloride (35.2 g) added dropwise. The mixture was then stirred for 2 hours and the solid which precipitated was filtered off, washed with water and recrystallised from ethanol to give 30.0 g of the desired product, mp 204°–206° C.

(b) 3-(4-Methylphenyl)-6-(2-chlorophenyl)-1,2-dihydro-1-methyl-1,2,4,5-tetrazine By the method of Example 1 stages (b) and (c), the above compound was prepared from the product of stage (a) of this Example. Mp 152°–154° C.

EXAMPLES 7–13

By methods analogous to that of Example 6, the following compounds were prepared:
7. 3-(4-Methylphenyl)-6-(2-chlorophenyl)-1,2-dihydro-1,2,4,5-tetrazine, mp 194°–197° C.
8. 3-t-Butyl-6-(2-chlorophenyl)-1,2-dihydro-1,2,4,5-tetrazine, mp 172°–174° C.
9. 3-t-Butyl-6-(2-chlorophenyl)-1,2-dihydro-1(or 2)-methyl-1,2,4,5-tetrazine, mp 105°–120° C.
10. 3-Phenyl-6-(2-chlorophenyl)-1,2-dihydro-1,2,4,5-tetrazine, mp 206°–210° C.
11. 3-(2-Fluorophenyl)-6-(2-chlorophenyl)-1,2-dihydro-1(or 2)-methyl-1,2,4,5-tetrazine, mp 95°–97° C.
12. 3-(3-Methylphenyl)-6-(2-chlorophenyl)-1,2-dihydro-1(or 2)-methyl-1,2,4,5-tetrazine, mp 163°–165° C.
13. 3-(2-Bromophenyl)-6-(2-chlorophenyl)-1,2-dihydro-1(or 2)-methyl-1,2,4,5-tetrazine, mp 102°–104° C.

EXAMPLE 14

3,6-Bis(2-chlorophenyl)-1,2,4,5-tetrazine

The dihydrotetrazine from Example 2 (8.0 g) was dissolved in glacial acetic acid (50 ml) and treated dropwise with stirring with a solution of sodium nitrite (2.0 g) in water (10 ml). The addition over the mixture was poured into water and the solid filtered off. Recrystallisation from ethyl acetate yielded the product, mp 179°–182° C.

EXAMPLES 15–18

By the method of Example 14, the following compounds were prepared by oxidation of the corresponding 1,2-dihydrotetrazines:
15. 3-t-Butyl-6-(2-chlorophenyl)-1,2,4,5-tetrazine, mp 86°–90° C.
16. 3-Phenyl-6-(2-chlorophenyl)-1,2,4,5-tetrazine, mp 120°–122° C.
17. 3-(2-Bromophenyl)-6-(2-chlorophenyl)-1,2,4,5-tetrazine, mp 166°–168° C.
18. 3-(4-Methylphenyl)-6-(2-chlorophenyl)-1,2,4,5-tetrazine, mp 129°–132° C.

EXAMPLE 19

Bis (α:2-dichlorobenzylidene)hydrazine (alternative method)

(a) Bis(2-chlorobenzylidene)hydrazine

Hydrazine hydrate (1,000 g) in water (2 l) and ethanol (2.4 l) was stirred at room temperature. 2-Chlorobenzoldehyde (5,620 g) in ethanol (2 l) was added dropwise over 3 hours at below 30° C. The mixture was then stirred for 2 hours at room temperature. Water (10 l) was added and the product was filtered off, washed with water and dried to give 5,402 g of the desired product.

(b) Bis(α:2-dichlorobenzylidene)hydrazine

The azine product of stage (a) (300 g) was suspended in acetic acid (1,350 ml) and acetic anhydride (150 ml). The stirred suspension was then cooled and chlorine was passed in, whilst maintaining the temperature at under 20° C. The azine dissolved and was replaced by a precipitate of the monochloroazine. At this stage cooling was stopped and the chlorination continued at room temperature until all the solid had dissolved. The mixture was then left at room temperature overnight. The crystalline precipitate was filtered off, washed with ethanol and dried in vacuo to give 257.5 g of desired product, mp 103°–105° C.

EXAMPLE 20

N-(α:2-dichlorobenzylidene)-N'-(α:2:4-trichlorobenzylidene)hydrazine (a) N-(α:2-dichlorobenzylidene)-N'-(2,4-dichlorobenzylidene)hydrazine N'-(2,4-dichlorobenzylidene)-N-2-chlorobenzoylhydrazine (21.2 g) was suspended in dichloroethane (160 ml) and the mixture was refluxed with stirring. Thionyl chloride (8.4 g) was added dropwise and the mixture was stirred and refluxed overnight. Half the solvent was evaporated off in vacuo and the remainder was left to crystallise. 14.4 g Of desired product, mp 86–91, were obtained.

(b) N-(α:2-dichlorobenzylidene)-N'-(α:2:4-trichlorobenzylidene)hydrazine

The product of stage (a) (18.5 g) was suspended in acetic acid (115 ml) and acetic anhydride (11.5 ml), and the mixture was heated to 50° C. A stream of chlorine gas was passed through the mixture to saturation. The mixture was then left overnight at room temperature, then the acetic acid and acetic anhydride were evaporated off in vacuo. The residue was dissolved in diethyl ether, and the ether solution was extracted with sodium bicarbonate, washed with water, and dried over magnesium sulphate. Evaporation of the ether gave an oil which solidified to give 7.6 g of the desired product, mp 45°–50° 1 C.

EXAMPLE 21

3,6-bis(2-Chlorophenyl)-1,2-dihydro-1-methyl-1,2,4,5-tetrazine (a) 2,5-bis(2-Chlorophenyl)thiadiazole bis(2-Chlorophenyl)hydrazine (30.9 g) in pyridine (250 ml) was treated with phosphorus pentasulphide (22.2 g) in portions. The mixture was refluxed for 12 hours, cooled and poured into ice/water (1 liter). The solid obtained was filtered off, washed with water and dried in vacuo, and was recrystallised from isopropanol to give 18.3 g of the desired product as colourless needles, mp 111°–113° C.

(a¹) 2,5-bis(2-Chlorophenyl)thiadiazole—alternative route

The dichloroazine product of Example 1(b) (103.8 g) in ethanol (500 ml) was treated with sodium sulphide nonahydrate (90.0 g), and the mixture was refluxed for 2 hours. It was then poured whilst still hot into ice/water (2 liters). The solid which formed was filtered off, washed with water and dried in vacuo to give 90.2 g of the desired product, mp 110°–112° C.

(b) 1,5-bis(2-Chlorophenyl)-3(or 4)-methylthiadiazolium sulphate

The product of stage (a) (16.0 g) and dimethyl sulphate (6.56 g) were heated together on a steam bath for 30 minutes and then cooled. The solid obtained was triturated with acetone, filtered off, washed with acetone, then with diethyl ether, and was then dried in vacuo to give 16.8 g of the desired product, mp 146°–148° C.

(c) 3,6-bis(2-Chlorophenyl)-1,2-dihydro-1-methyl-1,2,4,5-tetrazine

The product of stage (b) (6.0 g) was suspended in ethanol (30 ml) and hydrazine hydrate (1.5 g) was added. The mixture was refluxed for 50 minutes, cooled and filtered. The filtrates were evaporated to low volume and diluted with water to give a semi-solid which solidified on trituration. The solid was filtered off and dried in vacuo to give 3.1 g of desired product, mp 115°–116° C., identical to the product of Example 1.

EXAMPLE 22

3,6-bis(2-Chlorophenyl)-1,4-dihydro-1,4-dimethyl-1,2,4,5-tetrazine

The product of Example 21 stage (6) (6.0 g) was suspended in ethanol (30 ml) and methyl hydrazine (1.40 g) was added. The mixture was refluxed for 30 minutes, cooled and filtered. The filtrate was then evaporated to low volume and diluted with water. The solid which formed was filtered off, washed with water and dried in vacuo to give, on recrystallisation from petroleum ether (80°–100° C.), 3.40 g of desired product, mp 148°–149° C.

EXAMPLES 23–26

By methods analogous to those of Examples 21 and 22 the following compounds were prepared:
23. 3,6-bis(2-Chlorophenyl)-1,2-dihydro-1-ethyl-1,2,4,5-tetrazine, mp 106°–108° C.
24. 3,6-bis(2-Chlorophenyl)-1,4-dihydro-1-ethyl-4-methyl-1,2,4,5-tetrazine, mp 92°–94° C.
25. 3,6-bis(2-Chlorophenyl)-1,4-dihydro-1-(2-hydroxyethyl)-4-ethyl-1,2,4,5-tetrazine, mp 149°–152° C.

EXAMPLE 26

A 50% wettable powder formulation of the compound of Example 1 was prepared from the following:

|  | % w/w |
|---|---|
| Compound of Example 1 | 50 |
| Reax 45L (lignin based wetting and dispersing agent) | 5 |
| Polyfon H (sodium salt of sulphonated Kraft lignin, by Westvaco Corporation) | 2 |
| Neosyl (precipitated silica) | 10 |
| China Clay | 33 |

EXAMPLE 27

A 50% wettable powder formulation of the compound of Example 14 was prepared from the following:

|  | % w/w |
|---|---|
| Compound of Example 14 | 50 |
| Reax 45L | 5 |
| China clay | 45 |

EXAMPLE A

Aqueous acetone solutions containing 1,000, 300, 100, 10 and 3 ppm respectively of each of the compounds listed below together with 500 ppm of the wetting agent Lissapol NX (a nonylphenol/ethylene oxide condensate) were applied to 2 cm diameter discs cut from the leaves of french bean plants, *Phaseolus vulgaris*, each infested with 50–100 eggs of the greenhouse red spider mite, *Tetranychus telarius*. The treated leaf discs and mite eggs, together with controls treated with wetting agent alone were held at 25° C. for 5 days on moist filter paper. The percentage mortality of the mite eggs was then recorded, and the $LC_{50}$ was determined and scored according to the following scale:

| $LC_{50}$ (ppm) | Score |
|---|---|
| >1000 | 0 |
| 300–1000 | 1 |
| 100–299 | 2 |
| 30–99 | 3 |
| 10–29 | 4 |
| 3–9.9 | 5 |
| 1–2.9 | 6 |

The results obtained were as follows:

| Compound Example No | Score |
|---|---|
| 1 | 6 |
| 2 | 5 |
| 3 | 1 |
| 4 | 3 |
| 6 | 2 |
| 7 | 2 |
| 8 | 2 |
| 9 | 1 |
| 10 | 3 |
| 11 | 4 |
| 12 | 1 |
| 13 | 6 |
| 14 | 6 |
| 15 | 3 |
| 16 | 2 |
| 17 | 6 |
| 18 | 2 |

Control leaf discs treated with water and wetting agent alone gave less than 5% mortality over the same period.

EXAMPLE B

French bean plants with two fully expanded cotyledonary leaves were sprayed with aqueous acetone solutions respectively of the compounds of Examples 1 and 14 containing 1,000 ppm wt/vol active ingredient and 500 ppm of Lissapol NX. After 24 hours and at 7 day intervals up to 35 days, 2 cm discs were cut from the treated leaves, placed on a moist filter paper and each infested with 10 adult female mites, *Tetranychus cinnabarinus*. After 24 hours the mites were removed, by which time they had deposited about 100 eggs on each disc. The mortality of these eggs was measured after 5 days when it was observed that greater than 95% mortality occurred on each disc.

EXAMPLE C

Adjacent rows of young Top Red apple trees were managed until the European red mite (*Panonychus ulmi*) numbers started to increase. The trees were then sprayed with aqueous suspensions of a wettable powder containing, as active ingredient, the compound of Example 1. Different trees were then sprayed at a rate of 1.5 liters/tree with suspensions containing 250, 500 and 1,000 ppm respectively of active ingredient. Other trees were left untreated as controls. Counts were taken pretreatment and at roughly 7-day intervals of the numbers of mites present, a 60-leaf sample being counted each time without removal from the tree.

Results obtained, expressed as mean number of mites per leaf, were as follows:

| Treatment | Days after Treatment | | | | | | | | | |
|---|---|---|---|---|---|---|---|---|---|---|
| | 0 (Pre-count) | +7 | +14 | +21 | +28 | +35 | +42 | +49 | +55 | +62 |
| 250 ppm | 0.43 | 0.65 | 0.36 | 0.51 | 0.50 | 0.85 | 1.01 | 0.97 | 0.55 | 0.35 |
| 500 ppm | 0.73 | 1.35 | 1.01 | 0.96 | 1.08 | 1.25 | 1.20 | 1.43 | 0.93 | 0.78 |
| 1,000 ppm | 0.61 | 0.45 | 0.36 | 0.51 | 0.46 | 0.53 | 0.45 | 0.20 | 0.16 | 0.13 |
| 0 ppm (control) | 0.26 | 1.70 | 2.11 | 4.88 | 6.70 | 8.50 | 9.91 | 16.93 | 13.76 | 5.6 |

We claim:

1. A method of combatting acarids, their eggs or their larvae, which comprises applying to a site either infested or liable to infestation with them an effective amount of one or more substituted tetrazines of the formula:

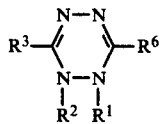

or of the formula:

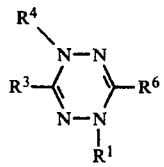

wherein $R^1$, $R^2$ and $R^4$, which may be the same or different, each represent hydrogen, phenyl, alkyl or 1 to 6 carbon atoms or alkenyl or alkynyl of 3 to 6 carbon atoms, each of which phenyl, alkyl, alkenyl or alkynyl groups may be unsubstituted or substituted by one or more halogen atoms, hydroxy groups, cyano groups, carboxy groups, alkoxycarbonyl groups of 2 to 5 carbon atoms or alkoxy groups of 1 to 4 carbon atoms; or $R^1$ and $R^2$ together represent a single bond; $R^3$ represents alkyl of 1 to 6 carbon atoms, cycloalkyl of 3 to 7 carbon atoms, phenyl, or phenylalkyl of 7 to 10 carbon atoms, each of which may be unsubstituted or substituted by one or more halogen atoms, alkyl or alkoxy groups of 1 to 6 carbon atoms, nitro groups, cyano groups, mercapto groups or alkylmercapto groups of 1 to 4 carbon atoms; and $R^6$ represents a phenyl group substituted in at least the 2-position by fluorine, chlorine, bromine or iodine.

2. An acaricidal, larvicidal or ovicidal composition which comprises from 0.5 to 99% by weight of one or more substituted tetrazines of formula I or formula II as defined in claim 1 in association with at least one of surface active agents and carriers.

3. A substituted tetrazine of the formula:

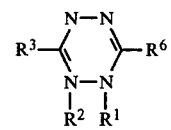

or of the formula:

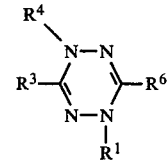

wherein $R^1$, $R^2$ and $R^4$, which may be the same or different, each represent hydrogen, phenyl, alkyl of 1 to 6 carbon atoms or alkenyl or alkynyl of 3 to 6 carbon atoms, each of which phenyl, alkyl, alkenyl or alkynyl groups may be unsubstituted or substituted by one or more halogen atoms, hydroxy groups, cyano groups, carboxy groups, alkoxycarbonyl groups of 2 to 5 carbon atoms or alkoxy groups of 1 to 4 carbon atoms; or $R^1$ and $R^2$ together represent a single bond; $R^3$ represents alkyl of 1 to 6 carbon atoms, cycloalkyl of 3 to 7 carbon atoms, phenyl, or phenylalkyl of 7 to 10 carbon atoms, each of which may be unsubstituted or substituted by one or more halogen atoms, alkyl or alkoxy groups of 1 to 6 carbon atoms, nitro groups, cyano groups, mercapto groups or alkylmercapto groups of 1 to 4 carbon atoms; and $R^6$ represents a phenyl group substituted in at least the 2-position by fluorine, chlorine, bromine or iodine; with the proviso that, in the compounds of formula I wherein $R^6$ represents 2-fluorophenyl, when $R^1$ and $R^2$ represent a single bond, $R^3$ does not represent methyl, trifluoromethyl or 2-fluorophenyl, and when $R^1$ and $R^2$ both represent hydrogen, $R^3$ does not represent trifluoromethyl.

4. A compound according to claim 3 wherein $R^1$ and $R^2$ or $R^1$ and $R^4$ each represent hydrogen or alkyl of 1 to 6 carbon atoms, optionally substituted by one or more hydroxy groups.

5. A compound according to claim 4 wherein one of $R^1$ and $R^2$ represents hydrogen and the other represents alkyl of 1 to 6 carbon atoms.

6. A compound according to claim 3 wherein $R^3$ represents unsubstituted alkyl of 1 to 6 carbon atoms, or phenyl which is unsubstituted or substituted by one or more halogen atoms, alkyl or alkoxy groups of 1 to 4 carbon atoms or nitro groups.

7. A compound according to claim 3 wherein $R^6$ represents 2-chlorophenyl or 2-bromophenyl.

8. A compound according to claim 7 wherein $R^3$ represents a group identical to $R^6$.

9. A compound according to claim 3 selected from the group consisting of:
3,6-bis(2-chlorophenyl)-1,2-dihydro-1-methyl-1,2,4,5-tetrazine,
3,6-bis(2-chlorophenyl)-1,2-dihydro-1,2,4,5-tetrazine,
3,6-bis(2-fluorophenyl)-1,2-dihydro-1-methyl-1,2,4,5-tetrazine,
3,6-bis(2-fluorophenyl)-1,2-dihydro-1,2,4,5-tetrazine,
3,6-bis(2-chlorophenyl)-1,2-dihydro-1-(2-hydroxyethyl)-1,2,4,5-tetrazine,
3-t-butyl-6-(2-chlorophenyl)-1,2-dihydro-1,2,4,5-tetrazine,
3-t-butyl-6-(2-chlorophenyl)-1,2-dihydro-1(or 2)-methyl-1,2,4,5-tetrazine
3-phenyl-6-(2-chlorophenyl)-1,2-dihydro-1,2,4,5-tetrazine,
3-(2-fluorophenyl)-6-(2-chlorophenyl)-1,2-dihydro-1(or 2)-methyl-1,2,4,5-tetrazine,
3-(2-bromophenyl)-6-(2-chlorophenyl)-1,2-dihydro-1(or 2)-methyl-1,2,4,5-tetrazine,
3-(3-methylphenyl)-6-(2-chlorophenyl)-1,2-dihydro-1(or 2)-methyl-1,2,4,5-tetrazine,
3-(4-methylphenyl)-6-(2-chlorophenyl)-1,2-dihydro-1,2,4,5-tetrazine,
3-(4-methylphenyl)-6-(2-chlorophenyl)-1,2-dihydro-1(or 2)-methyl-1,2,4,5-tetrazine,
3,6-bis(2-chlorophenyl)-1,2,4,5-tetrazine,
3-t-butyl-6-(2-chlorophenyl)-1,2,4,5-tetrazine,
3-phenyl-6-(2-chlorophenyl)-1,2,4,5-tetrazine,
3-(2-bromophenyl)-6-(2-chlorophenyl)-1,2,4,5-tetrazine,
3-(4-methylphenyl)-6-(2-chlorophenyl)-1,2,4,5-tetrazine,
3,6-bis(2-chlorophenyl)-1,4-dihydro-1,4-dimethyl-1,2,4,5-tetrazine,
3,6-bis(2-chlorophenyl)-1,4-dihydro-1-(2-hydroxyethyl)-4-ethyl-1,2,4,5-tetrazine, and
3,6-bis(2-chlorophenyl)-1,4-dihydro-1-ethyl-4-methyl-1,2,4,5-tetrazine.

10. A compound according to claim 3 wherein $R^3$ represents a group identical to $R^6$.

11. A compound according to claim 3 wherein $R^3$ represents cyclohexyl.

12. A compound according to claim 3 which is of formula (I) wherein $R^1$ and $R^2$ both represent hydrogen, or together represent a single bond, or one represents hydrogen while the other represents methyl, $R^6$ represents 2-chlorophenyl or 2-bromophenyl and $R^3$ repesents T-butyl, phenyl, 2-chlorophenyl, 2-fluorophenyl, 2-bromophenyl, 3-methylphenyl or 4-methylphenyl.

13. A compound according to claim 3 which is 3,6-bis(2-chlorophenyl)-1,2-dihydro-1-methyl-1,2,4,5-tetrazine.

14. A compound according to claim 3 which is 3,6-bis(2-chlorophenyl)-1,2,4,5-tetrazine.

* * * * *